US009089291B2

(12) United States Patent
Copland

(10) Patent No.: US 9,089,291 B2
(45) Date of Patent: Jul. 28, 2015

(54) SYSTEM AND METHOD FOR OCULAR ABERROMETRY AND TOPOGRAPHY USING PLENOPTIC IMAGING

(71) Applicant: AMO Wavefront Sciences, LLC., Santa Ana, CA (US)

(72) Inventor: Richard J. Copland, Albuquerque, NM (US)

(73) Assignee: AMO WAVEFRONT SCIENCES, LLC, Santa Ana, CA (US)

( * ) Notice: Subject to any disclaimer, the term of this patent is extended or adjusted under 35 U.S.C. 154(b) by 0 days.

(21) Appl. No.: 14/198,334

(22) Filed: Mar. 5, 2014

(65) Prior Publication Data

US 2014/0268044 A1   Sep. 18, 2014

Related U.S. Application Data

(60) Provisional application No. 61/798,880, filed on Mar. 15, 2013.

(51) Int. Cl.
*A61B 3/14*   (2006.01)
*A61B 3/00*   (2006.01)
*A61B 3/107*   (2006.01)

(52) U.S. Cl.
CPC .. *A61B 3/14* (2013.01); *A61B 3/107* (2013.01)

(58) Field of Classification Search
CPC ............ A61B 3/14; A61B 3/12; A61B 3/103; A61B 3/152; A61B 3/113; A61B 3/1208; A61B 3/1225; A61B 3/024; A61B 3/032; A61B 3/1015
USPC ................ 351/206, 200, 205, 208–210, 218, 351/221–223, 246, 211
See application file for complete search history.

(56) References Cited

U.S. PATENT DOCUMENTS

| 4,665,913 A | 5/1987 | L'Esperance, Jr. |
| 4,669,466 A | 6/1987 | L'Esperance |
| 4,732,148 A | 3/1988 | L'Esperance, Jr. |
| 4,764,930 A | 8/1988 | Bille et al. |
| 4,770,172 A | 9/1988 | L'Esperance, Jr. |
| 4,773,414 A | 9/1988 | L'Esperance, Jr. |
| 5,108,388 A | 4/1992 | Trokel et al. |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |
| 5,993,438 A | 11/1999 | Juhasz et al. |
| 2012/0069298 A1* | 3/2012 | Ng .................................. 351/206 |
| 2013/0027512 A1* | 1/2013 | Aronsson et al. ............... 348/42 |
| 2014/0313515 A1* | 10/2014 | Hogan ........................... 356/479 |

* cited by examiner

*Primary Examiner* — Dawayne A Pinkney

(57) ABSTRACT

Improved systems and methods for ocular topography and using a plenoptic detector are provided. For example, a multifunction ocular topography and aberrometry system can comprise a first set of light sources, a second light source, a plenoptic detector and a processing system coupled to the plenoptic detector. The first set of light sources and the second light source are configured to selectively illuminate an eye. The plenoptic detector is configured to selectively receive images of the first set of light sources reflected from a corneal surface of the eye and generate first plenoptic image data representing the images of the first set of light sources. The plenoptic detector is further configured receive images of the second light source reflected from a retina of the eye and generate second plenoptic image data representing the images of the second light source.

34 Claims, 9 Drawing Sheets

SYSTEM AND METHOD FOR OCULAR ABERROMETRY AND TOPOGRAPHY USING PLENOPTIC IMAGING

CROSS-REFERENCES TO RELATED APPLICATIONS

This application claims priority to U.S. Provisional application No. 61/798,880, filed on Mar. 15, 2013, the entire contents of which are incorporated herein by reference.

TECHNICAL FIELD

Embodiments of the present invention generally relate to vision techniques, and particularly to techniques for ocular aberrometry and topography.

BACKGROUND OF THE INVENTION

Many modern ophthalmic surgical procedures require accurate measurements of the eye. For example, measurements of aberrations of the eye are important for the diagnosis and treatment of visual defects and acuity. Furthermore, there are a growing number of ways that aberrations can be corrected using both surgical and non-surgical means. Many of these methods rely on accurate, precise measurements of the whole ocular system so that patients may be screened, the corrective means applied and tested, and follow-up care provided as appropriate.

One type of ocular measurement is generally referred to as ocular topography. In general, ocular topography is the measurement of the surfaces in an ocular system. For example, ocular topography can include the determination of the surface shapes of the cornea and lens. Each of these measurements can be useful in various surgical and non-surgical treatments, and improved accuracy and precision of these measurements may lead to improved methods for correcting visual defects, and for identifying patients in need of care.

Another type of ocular measurement is generally referred to as aberrometry. In general, aberrometry is the measurement of the effects of aberrations or refractive errors in the eye. Thus, aberrometry can provide a measurement of the optical quality of the eye, including the overall quality and local variations in quality. Typically, aberrometers can measure spherical and cylindrical aberrations. Some aberrometers can additionally measure higher order aberrations. Again, each of these measurements can be useful in various surgical and non-surgical treatments, and improved accuracy and precision of these measurements may lead to improved methods for correcting visual defects, and for identifying patients in need of care.

A variety of newer multifunction devices have become available that can measure both ocular topography and aberrometry. However, these multifunction devices can suffer from a variety of issues. For example, the accuracy of multifunction devices can be impaired without precise alignment between the different imaging devices used for ocular topography and aberrometry. Such precise alignment can usually be accomplished through calibration and the use of measured offsets, but in some cases misalignment may still occur and result in impaired accuracy. Furthermore, the use of two imaging devices can result in imaging at slightly different angles, with the possible result of impaired accuracy.

For these and other reasons there is a continuing need for improved ocular topography and aberrometry devices and techniques.

BRIEF SUMMARY OF THE INVENTION

Embodiments of the present invention generally provide improved systems and methods for ocular topography and aberrometry. These systems and methods can be used to improve the effectiveness of a wide variety of different ophthalmic diagnostic procedures, and various surgical and non-surgical treatments. One embodiment provides a system and method for determining ocular topography and aberrometry data for the eye using a plenoptic detector. For example, a multifunction ocular topography and aberrometry system can comprise a first set of light sources, a second light source, a plenoptic detector and a processing system coupled to the plenoptic detector. The first set of light sources and the second light source are configured to selectively illuminate an eye. The plenoptic detector is configured to selectively receive images of the first set of light sources reflected from a corneal surface of the eye and generate first plenoptic image data representing the images of the first set of light sources. The plenoptic detector is further configured to receive images of the second light source reflected from a retina of the eye and to generate second plenoptic image data representing the images of the second light source. A processing system is coupled to the plenoptic detector and is configured to selectively analyze the first plenoptic image data to determine topography data for the eye and to analyze the second plenoptic image data to determine aberrometry data for the eye.

Thus, the system and method can determine ocular topography and aberrometry using one plenoptic detector. The use of one plenoptic detector to provide data for both ocular topography and aberrometry negates the need for precise alignment between separate detectors. Thus, the system and method can provide both accurate ocular topography and aberrometry.

To facilitate this, the plenoptic detector is configured to capture the intensity, position and direction of light hitting the detector. This information can be used to effectively refocus a plenoptic image at different focus depths after the image has been taken. The processing system can then use such a process to extract depth information from the plenoptic image. For example, by calculating distances between images reflected from different eye surfaces. From this, the processing system determines topography and aberrometry data for the eye.

The plenoptic detector includes a photosensor array comprising a plurality of photosensors and a microlens array comprising a plurality of lenslets. The microlens array is configured to receive images of the light sources reflected from surfaces of the eye and direct the images to the photosensor array. Such an arrangement allows the plenoptic detector to determine both the intensity and the direction of light hitting the detector.

The above summary and the following detailed description are merely exemplary, illustrative, and explanatory, and are not intended to limit, but to provide further explanation of the invention as claimed. Additional features and advantages of the invention will be set forth in the ensuing detailed descriptions that follow, and in part, will be apparent from the description, or may be learned by practicing various embodiments of the invention. The objectives and other advantages of the invention will be realized by the structures and methods particularly pointed out in the written description and claims as well as the accompanying drawings.

DETAILED DESCRIPTION OF THE INVENTION

Figure 1:
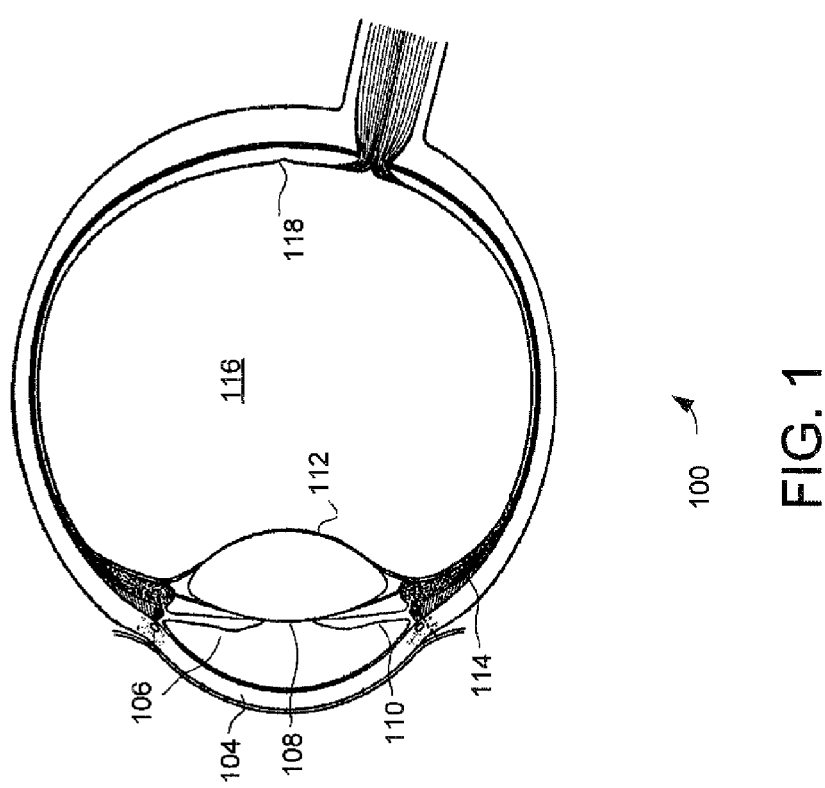
FIG. 1 is a cross-sectional side view of a human eye.

The figures and descriptions of the present invention have been simplified to illustrate elements that are relevant for a clear understanding of the present invention, while eliminating, for the purpose of clarity and brevity, many other elements found in typical ophthalmic techniques, systems, methods, lenses, and implantable optic apparatuses. Those of ordinary skill in the art may thus recognize that other elements and/or steps are desirable and/or required in implementing the present invention. However, because such elements and steps are well known in the art, and because they do not necessarily facilitate a better understanding of the present invention, those elements and steps are not discussed. This disclosure is directed to all applicable variations, changes, and modifications known to those skilled in the art. As such, the following detailed descriptions are merely illustrative and exemplary in nature and are not intended to limit the embodiments of the subject matter or the uses of such embodiments. As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, brief summary, or the following detailed description.

Embodiments of the present invention generally provide improved systems and methods for ocular topography and aberrometry. These systems and methods can be used to improve the effectiveness of a wide variety of different ophthalmic diagnostic procedures, and various surgical and non-surgical treatments. One embodiment provides a system and method for determining ocular topography and aberrometry data for the eye using a plenoptic detector. For example, a multifunction ocular topography and aberrometry system can comprise a first set of light sources, a second light source, a plenoptic detector and a processing system coupled to the plenoptic detector. The first set of light sources and the second light source are configured to selectively illuminate an eye. The plenoptic detector is configured to selectively receive images of the first set of light sources reflected from a corneal surface of the eye and generate first plenoptic image data representing the images of the first set of light sources. The plenoptic detector is further configured to receive images of the second light source reflected from a retina of the eye and to generate second plenoptic image data representing the images of the second light source. A processing system is coupled to the plenoptic detector and is configured to selectively analyze the first plenoptic image data to determine topography data for the eye and to analyze the second plenoptic image data to determine aberrometry data for the eye.

Thus, the system and method can determine ocular topography and aberrometry using one plenoptic detector. The use of one plenoptic detector to provide data for both ocular topography and aberrometry negates the need for precise alignment between separate detectors. Thus, the system and method can provide both accurate ocular topography and aberrometry.

Turning to the drawings, FIG. 1 illustrates a simplified cross-sectional view of an exemplary human eye 100. In general, the eye 100 includes a cornea 104, an anterior chamber 106, a pupil 108, an iris 110, a lens 112, a ciliary muscle 114, a posterior chamber 116, and a retina 118. As briefly described earlier, many modern ophthalmic procedures require accurate measurements of the whole ocular system so that patients may be properly screened and treated. One type of ocular measurement is generally referred to as ocular topography, where ocular topography is the measurement of the surfaces in an ocular system. For example, ocular topography can include the determination of the surface shapes of the cornea 104 and lens 112. Another type of ocular measurement is generally referred to as aberrometry. In general, aberrometry is the measurement of the effects of aberrations or refractive errors in the eye 100. Typically, aberrometers can measure spherical and cylindrical aberrations, and some aberrometers can additionally measure higher order aberrations. Each of these various measurements can be useful in diagnosis and treatment, including surgical and non-surgical treatments. Furthermore, improved accuracy and precision of these measurements may lead to enhanced methods for correcting visual defects.

Figure 2:
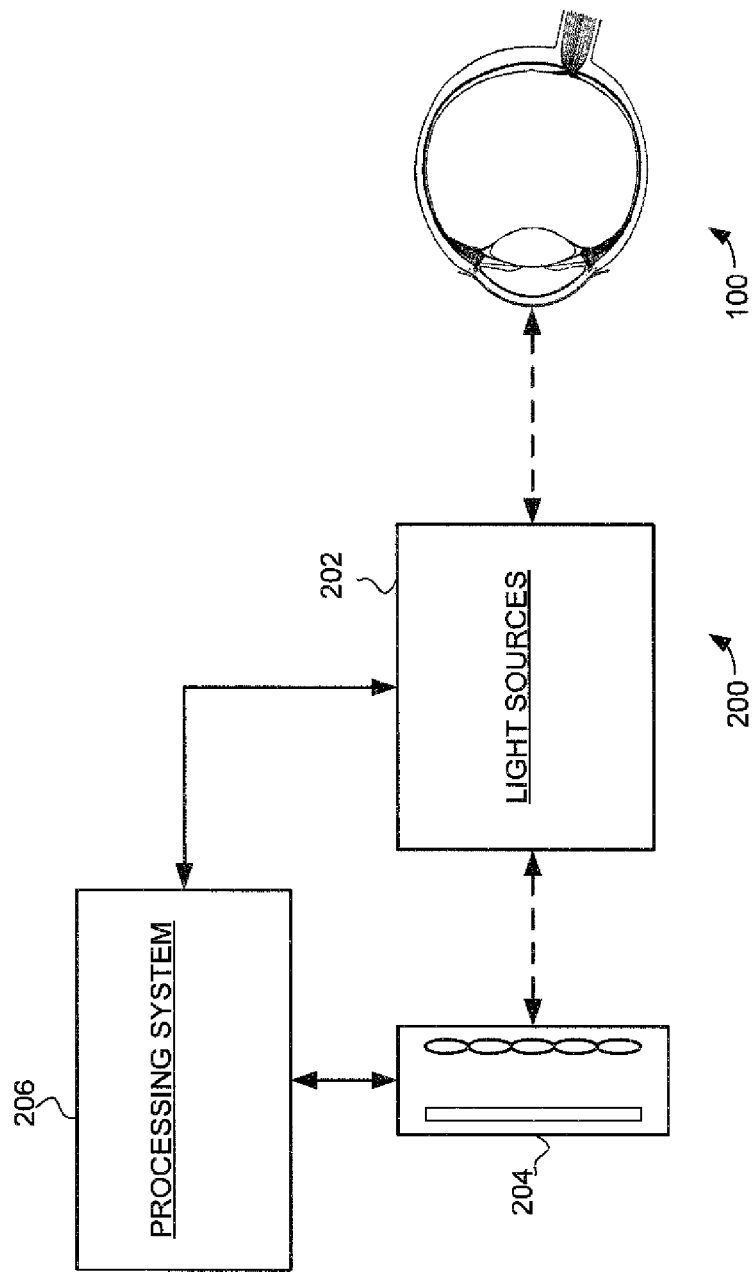
FIG. 2 is a schematic diagram of an ocular topography and aberrometry system in accordance with an embodiment of the invention.

Turning now to FIG. 2, a simplified schematic view of an ocular topography and aberrometry system 200 is illustrated. The system 200 includes light sources 202, a plenoptic detector 204, and a processing system 206. In general, the light sources 202 and associated optical elements (not shown in FIG. 2) are configured to illuminate the eye 100 with a set of light sources. In one embodiment the set of light sources comprises a first set of light sources and a second light source, where the first set of light sources is configured to cause images to be reflected from corneal surfaces while the second light source is reflected off the retina. In this case, the first set of light sources can comprise a pattern that includes a plurality of common elements and at least one reference element. For example, the first set of light sources can comprise a Placido-type light source and reference elements in a center portion. Likewise, the second light source can comprise a variety of different types of sources. In one specific example, the second light source can comprise a super luminescence diode (SLD). As will be described in greater detail below, other suitable light sources can be used as well.

In general, the plenoptic detector 204 is configured to detect the resulting images on the eye 100. Specifically, the plenoptic detector 204 is configured to determine both intensity and direction of light reflecting from the eye 100 and hitting the detector. This information can be used to effectively refocus a plenoptic image at different focus depths after the image has been captured, and this refocusing can be used to extract depth information. For example, by calculating distances between images reflected from different eye surfaces. Furthermore, this directional information can be used to determine the direction of light rays emanating from the eye.

As one example implementation, the plenoptic detector 204 can include a photosensor array comprising a plurality of photosensors and a microlens array comprising a plurality of microlenses that are referred to as lenslets. In such a configuration the microlens array is configured to receive images of the light sources 202 reflected from surfaces of the eye 100 and direct the images to the photosensor array. From this, the plenoptic detector 204 can calculate both intensity and direction of light hitting the plenoptic detector 204.

In the embodiment shown in FIG. 2, the light sources 202 and plenoptic detector 204 are each coupled to processing system 206. The processing system 206 is configured to control the light sources 202 and plenoptic detector 204. Additionally, the processing system 206 is configured to analyze the plenoptic image data to determine topography and aberrometry data for the eye 100. As described above, the plenoptic detector 204 is configured to capture the intensity, position and direction of light hitting the detector. The processing system 206 can use this plenoptic image data to refocus captured images at different focus depths after the images have been taken. The processing system 206 can then use such a process to extract depth information from the plenoptic image. For example, the processing system 206 can be implemented to calculate distances between images reflected from different eye surfaces. From this, the processing system 206 can determine topography and aberrometry data for the eye. To facilitate these and other actions the processing system 206 can comprise any suitable configuration of processing elements, including various computer memories, controllers, and other devices. For example, the processing system 206 can be implemented as software residing in memory and being executed by a processor, or as hardware hardcoded into a processing device, or any combination thereof.

As specific examples, the processing system 206 can be configured to analyze the first plenoptic image data to determine topography data for the eye by calculating dimensions of shapes in the images of the first set of light sources reflected from the corneal surface of the eye. In another example, the processing system 206 is configured to analyze the first plenoptic image data to determine topography data for the eye by calculating a distance to the corneal surface using depth information generated from the first plenoptic image data. In another example, the processing system 206 is configured to analyze the first plenoptic image data to determine topography data for the eye by calculating a distance to the corneal surface using depth information generated from the first plenoptic image data and using the calculated distance to determine a base radius of the corneal surface. In another example, the processing system 206 is configured to analyze the first plenoptic image data to determine topography data for the eye by reconstructing image data. In another example, the processing system 206 is configured to analyze the first plenoptic image data to determine topography data for the eye by using a first image taken with a small aperture and calculating a distance to the corneal surface using depth information generated from the first plenoptic image data of the first image, and by using a second image taken without the small aperture to reconstruct the image data. In another example, the processing system 206 is configured to analyze the second plenoptic image data to determine aberrometry data for the eye by calculating angles of light emanating from the eye using the second plenoptic image data. In another example, the processing system 206 is configured to analyze the second plenoptic image data to determine aberrometry data for the eye by using direction information in the second plenoptic image data to determine angles of light emanating from the eye. In another example, the processing system 206 is configured to analyze the second plenoptic image data to determine aberrometry data for the eye by calculating dimensions of shapes in the images of the second light source.

As noted above, in some embodiments topography data is calculated by reconstructing a shape of the cornea from the plenoptic image data. In general, such reconstruction can be performed using any suitable reconstruction technique. For example, many different techniques have been described for reconstructing corneal shape from data generated by wavefront aberrometers. Likewise, different techniques for reconstructing corneal shapes from corneal images have been described. These various techniques can be implemented to reconstruct corneal shapes from plenoptic image data, using the intensity and direction information provided by the plenoptic camera.

As noted above, the light sources 202 can comprise any source of electromagnetic radiation, particularly a source in or near the visible band of the electromagnetic spectrum, for example, in the infrared, near infrared, or ultraviolet bands of the electromagnetic radiation. Furthermore, as used herein, the term "light" may be extended to mean electromagnetic radiation in or near the visible band of the electromagnetic spectrum, for example, in the infrared, near infrared, or ultraviolet bands of the electromagnetic radiation, or to mean electromagnetic radiation detectible by a photodetector or electromagnetic image sensor (e.g. CCD) or that is otherwise useful in measuring the optical or physical characteristics of an object under examination.

In one embodiment the light sources 202 may include a pattern of shapes arranged in a grid. For example, in one embodiment, the light sources 202 are configured in a pattern that includes a plurality of common elements having a common form and one or more reference elements having a reference form that is different than the common form. As used herein, the term "form", when applied to an element or object, means the shape and orientation of the element or object, without regard to its scale or dimension. As used herein the term "different", when applied to a comparison between two or more "forms", means the forms being compared have a different shape and/or orientation in comparison to one another. As used herein the term "same", when applied to a comparison between two or more "forms", means the forms being compared have equivalent shape and orientation in comparison to one another.

In one embodiment that will be described in greater detail below, the light sources 202 further include a Helmholtz source. The light sources 202 may also include additional light sources that are not generally used for topography and aberrometry, but may be used for other purpose, for example, to control a pupil size.

In another embodiment the light sources 202 may be configured in a Placido-type source. As used herein, the term "Placido-type source" means a mask, pattern, or plurality of individual light sources disposed such that light from the source(s) reflects off of a reference or test object, passes through an imaging system, and is received by a detector, wherein light from the Placido-type source passes only once through the imaging system. In this embodiment, the individual light sources may be active sources generating light energy or apertures through which light energy is transmitted. Individual mask or pattern features may include lighter or more reflective portions of the mask or pattern configured to reflect light. As used herein, the term "Placido disk" means a Placido-type source configured as a plurality of concentric rings or annular shapes.

In one specific example, the light sources 202 are configured to generate Purkinje images on different surfaces in the eye 100, and the processing system 206 is configured to determine topography and aberrometry data using the Purkinje images. As more specific examples, the light sources can be arranged in a circle or semicircle, and these Purkinje images can include a Purkinje I image from light reflected from an outer surface of a cornea in the eye 100 and a Purkinje II image from light reflected from an inner surface of the cornea in the eye.

The system 200 can be implemented as a stand-alone device or as part of a larger diagnostic system or a larger ophthalmic laser system. For example, the system 200 can be implemented as part of an ophthalmic diagnostic and/or measurement system designed to provide one or more of wavefront aberrometry, topography, autorefractometry, pupillometry, optical coherence topography and aberrometry. More specifically, the system 200 may be incorporated into and implemented as part of the Abbott WaveScan WaveFront™ System, an ophthalmic diagnostic and measurement system that uses a Shack-Hartmann wavefront sensor to quantify aberrations throughout the entire optical system of the patient's eye, including second-order aberrations related to spherical error and cylindrical errors and higher order aberrations related to coma, trefoil, and spherical aberrations. An exemplary wavefront diagnostic system is described in U.S. Pat. No. 7,931,371, issued to Dai, which is incorporated by reference in its entirety.

Alternatively, the system 200 may be incorporated into and implemented as part of a device or system that is used to generate pulsed laser beams, including non-ultraviolet (non-UV), ultrashort pulsed laser beams that have pulse durations that are measured in femtoseconds, as described in U.S. Pat. Nos. 4,764,930 and 5,993,438. Certain non-UV, ultrashort pulsed laser systems are used for ophthalmic surgeries. For example, U.S. Pat. No. 5,993,438 discloses a laser device for performing ophthalmic surgical procedures to effect high-accuracy corrections of optical aberrations. Further details of suitable systems for performing laser ophthalmic procedures can be found in commonly-assigned U.S. Pat. Nos. 4,665,913, 4,669,466, 4,732,148, 4,770,172, 4,773,414, 5,207,668, 5,108,388, 5,219,343, 5,646,791 and 5,163,934.

Figure 3:
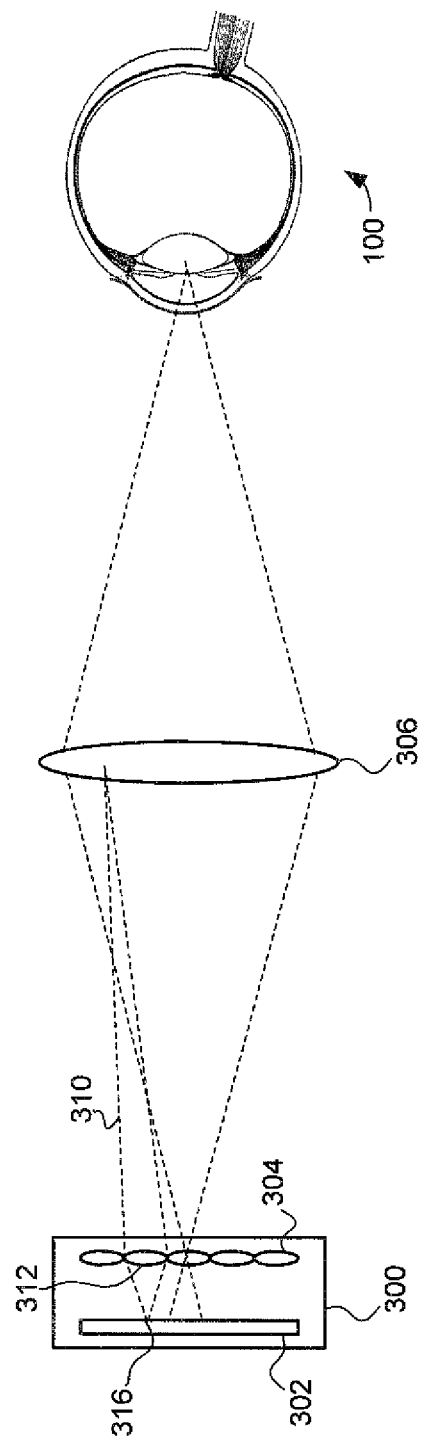
FIG. 3 is a schematic diagram of a plenoptic detector and an eye in accordance with an embodiment of the invention.

Turning now to FIG. 3, a plenoptic detector 300 is illustrated schematically. The plenoptic detector 300 includes a photosensor array 302 comprising a plurality of photosensors and a microlens array 304 comprising a plurality of microlenses, with individual microlenses sometimes referred to as lenslets. In the illustrated embodiment, the microlens array 304 is configured to receive images of the light sources (not shown in FIG. 3) reflected from surfaces of the eye 100 and directed to the detector 300 with lens 306. In general, each lenslet in the microlens array 304 covers multiple sensors or "pixels" in the photosensor array 302. As will be described in greater detail below, this results in reduced spatial resolution, but also provides the ability to determine direction information for incident light hitting the plenoptic detector 300.

A variety of different types of devices can be used for the photosensor array 302 in the plenoptic detector 300. For example, the individual photosensors can be implemented with digital imaging devices such as a charge coupled detector (CCD). As another example, the photosensors can be implemented with active pixel sensors. Likewise, the microlens array can be implemented in a variety of different ways. For example, the microlens array can be manufactured by photolithographic or molding processes. Furthermore, different relative positioning between the various elements can be used. For example, in some plenoptic detectors 300 the microlens array 304 is positioned to be in the image plane of the main lens 306. Conversely, in other examples the microlens array 304 is positioned to be in front of or behind the image plane of the main lens 306. Likewise, different relative positions between the microlens array 304 and the photosensor array 302 can be used. For example, the photosensor array 302 may be positioned one lenslet focal length behind the microlens array 304.

Next, it should be noted that because each lenslet in microlens array 304 covers multiple pixels in the photosensor array 302, the resulting images captured by the photosensor effectively have reduced spatial image resolution, while adding the ability to determine directional information. As one example, each lenslet in the microlens array 304 may correspond to 100 pixels in the photosensor array 302. In such an embodiment the resulting images would be reduced in spatial resolution by two orders of magnitude. Again, this is just one example, and in other cases each lenslet could correspond to more or fewer pixels on the photosensor array 302. For example, some plenoptic detectors 300 may use 10 pixels per lenslet in the microlens array 302, and would thus have less reduction in resolution. However, such plenoptic detectors 300 would also provide reduced directional information. And while the reduction in resolution may be considered undesirable for some applications, the embodiments described herein use such plenoptic image data to determine information about an eye that could not be determined with an ordinary camera regardless of the increased resolution.

In general, the plenoptic detector 300 as illustrated in FIG. 3 is configured to determine both intensity and direction of light reflecting from the eye 100 and hitting the detector 300. To accomplish this, the lens 306 is configured to direct light reflected from surfaces of the eye 100 to the microlens array 304. The microlens array 304 is configured to receive this light and direct that light to the photosensor array 302. From this, the plenoptic detector 300 can calculate both the intensity and direction of the light reflected from the eye 100.

In general, each lenslet in the microlens array 304 receives light from the eye at a different angle than the other lenslets in the array, and each photosensor in the photosensor array 302 receives a different view of the eye from each lenslet in the array of microlenses 304, wherein each different view of the eye is received at a separate location on the photosensor array 302 to produce a multidimensional array of different views of the eye at the photosensor array 302. Stated another way, each lenslet in the microlens array 304 receives light from the eye at different angles and spatially separates the light at different angles at the photosensor array 302. Stated yet another way, each lenslet in the microlens array 304 is configured such that light arriving at a point in different directions is directed at a different point on the photosensor array 302 such that direction information for the light ray can be determined from a position of the light ray Conventional cameras capture two-dimensional images, with each pixel in the image representing the total amount of light striking each point in the camera sensor. Notably, a conventional two-dimensional image does not include any information about the direction any of the light was traveling when it hit the sensor. In contrast, a plenoptic detector such as detector 300 captures information on the directional distribution of the light rays.

Specifically, the microlens array 304 enables the plenoptic detector 300 to capture the light-field, i.e. to record not only image intensity, but also the distribution of intensity in different directions at each point. Specifically, the rays at the microlens array 304 have different angles, and passing through a lenslet causes rays with different angles to separate. Thus, each lenslet in the microlens array 304 splits a beam coming to it from the main lens 306 into different rays, and each of these different rays hits a different pixel on photosensor array 302. The result is a multipixel image formed under each lenslet in the microlens array 304, with the multipixel image containing measurements of different angular samples of the incident light at the lenslet. This multipixel area under each lens may be referred to as a "macropixel", and the plenoptic detector 300 effectively generates a "microimage" at each such macropixel. For example, a plenoptic detector with 100,000 lenslets in the microlens array 304 will contain 100,000 macropixels, and thus generate 100,000 microimages.

An example of this is illustrated in FIG. 3, which shows rays 310 hitting lenslet 312 in microlens array 304, and subsequently hitting a point 316 on photosensor array 302. For clarity, only rays through lenslet 312 are illustrated, but other rays through different lenslets would also fall at different pixels on the photosensor array 302. The result is a microimage at each macropixel, and the raw image data of the plenoptic detector 300 could thus be considered an array of such microimages.

Stated another way, each lenslet in the microlens array 304 functions to convert directional or angular information into positional information that is captured at the photosensor array 302. Because of this conversion, the position of a ray at the photosensor array 302 provides directional or angular information about the ray. Thus, the measurements taken at the pixels in the photosensor array 302 can be used to provide both directional and intensity data regarding light reflected from the eye 100. And such measurements, as a set of such plenoptic image data, can be used to form an image by selecting appropriate pixels from each microimage. Furthermore, by mixing pixels from different microimages, images at different focus depths can be generated.

Figure 4:
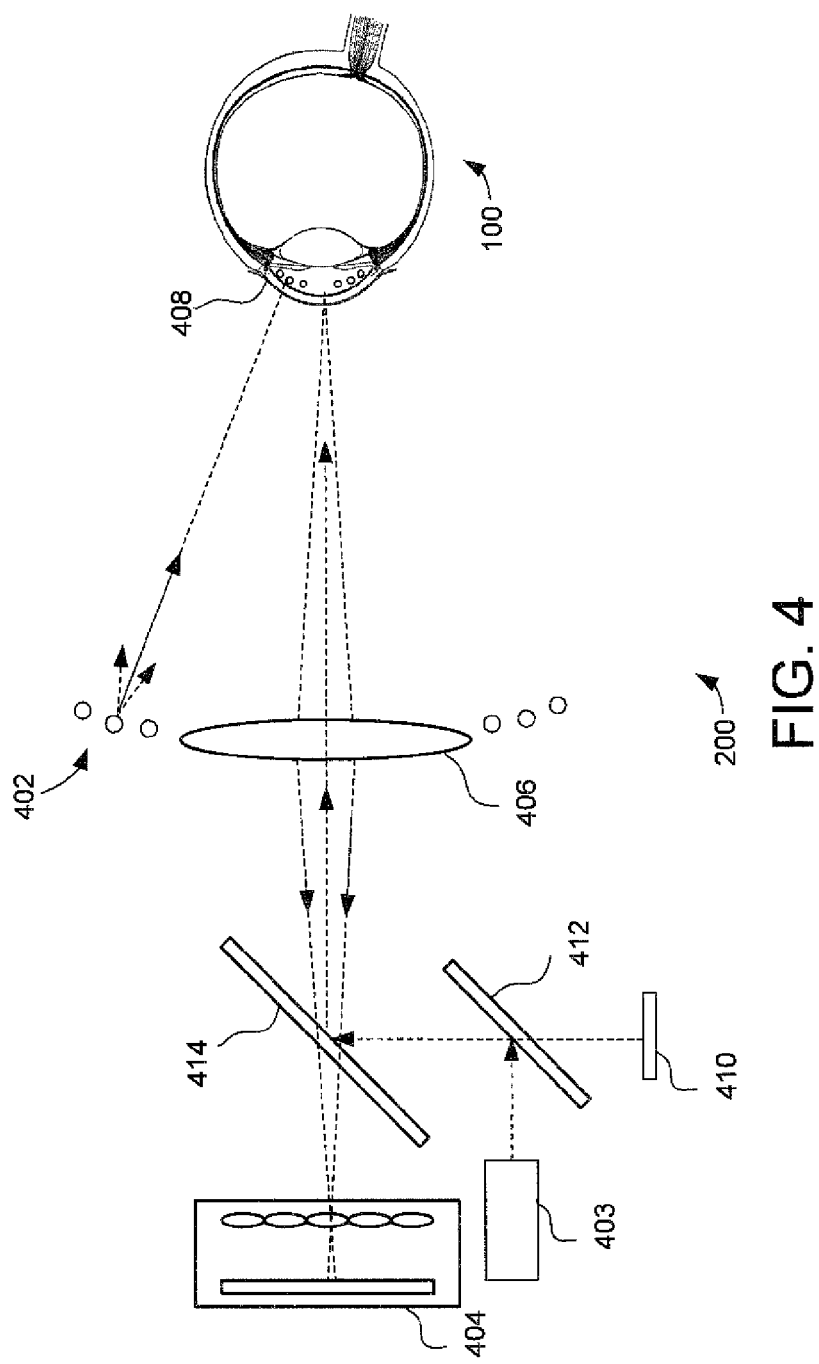
FIGS. 4-9 are schematic diagrams of ocular topography and aberrometry systems in accordance with embodiments of the invention.

Turning now to FIG. 4, a simplified schematic view of an ocular topography and aberrometry system 400 is illustrated. The system 400 includes a first set of light sources 402, a second light source 403, a plenoptic detector 404, a lens 406, a target 410, a first beam splitter 412 and a second beam splitter 414. Not shown is a processing system that would be coupled to at least the plenoptic detector 404. The target 410 is generally used to give the patient a point of focus that is far away, thus drawing out the focus of the eye 100. It should be noted that in this illustrated embodiment the eye 100 is more than one focal length away from the lens 406.

In general, the first set of light sources 402 and the lens 406 are configured to illuminate the eye 100, and specifically to illuminate corneal surfaces of the eye. In this case the first set of light sources 402 can comprise light emitting diodes (LEDs) or other such light sources arranged in a semicircle and configured to illuminate the eye 100 to generate Purkinje images 408 on different surfaces in the eye. Likewise, the second light source 403, the first beam splitter 412 and the second beam splitter 414 are configured to illuminate the eye 100, and in particular the retina of the eye 100. In this case the second light source can comprise a super luminescent diode (SLD) or other such light source. In such a configuration the SLD provides more than one wavelength over a relatively narrow range.

Thus, the first light sources 402 are specifically configured to illuminate corneal surfaces of the eye to generate Purkinje images 408 on different surfaces in the eye, where the light from the Purkinje images is collected by lens 406 and passed to the plenoptic detector 404. Thus, in general, the first light sources 402 are used to determine topography. The second light source 403 is configured to travel to the retina in the eye 100. When the light hits the retina it scatters in all directions, with some light coming back out parallel where it is collected by the lens 406 and passed to the plenoptic detector 404. Thus, in general, this second light source 403 is used for aberrometry.

Again, the plenoptic detector 404 is configured to detect the resulting images on the eye 100. Specifically, the plenoptic detector 404 is configured to receive images of the first set of light sources 402 reflected from a corneal surface of the eye and generate first plenoptic image data representing the images of the first set of light sources 402. Likewise, the plenoptic detector 404 is configured to receive images of the second light source 403 reflected from the retina of the eye and generate second plenoptic image data representing the images of the second light source. In both cases the plenoptic detector 404 is configured to measure both intensity and direction of light reflecting from the eye 100 and hitting the detector 404.

As more specific examples, the Purkinje images 408 can include a Purkinje I image from light reflected from an outer surface of the cornea in the eye 100, a Purkinje II image from light reflected from an inner surface of the cornea in the eye 100, a Purkinje III image from light reflected from an anterior surface of the lens in the eye 100, and a Purkinje IV image from light reflected from a posterior surface of the lens in the eye 100.

The processing system (not shown in FIG. 4) is coupled to the plenoptic detector 404 and configured to selectively analyze the first plenoptic image data to determine topography data for the eye and analyze the second plenoptic image data to determine aberrometry data for the eye. In general, this can be done by processing the first plenoptic image data and the second plenoptic image data to refocus the reflected light at the different focus depths that correspond to different images and different positions on those images. This refocusing can be used to extract depth information, specifically to calculate the shapes, sizes and distances of the images, and distances between images. From this, the processing system can determine topography and aberrometry data for the eye.

As noted above, in the system 400 the eye 100 is located at more than one focal length from the first lens. This generally provides the best arrangement for obtaining depth information. However, this can reduce the imaging accuracy and the aberrometry measurement, but the plenoptic data may also be used to adjust the collected image to determine the equivalent light field at the object plane of the eye.

Figure 5:
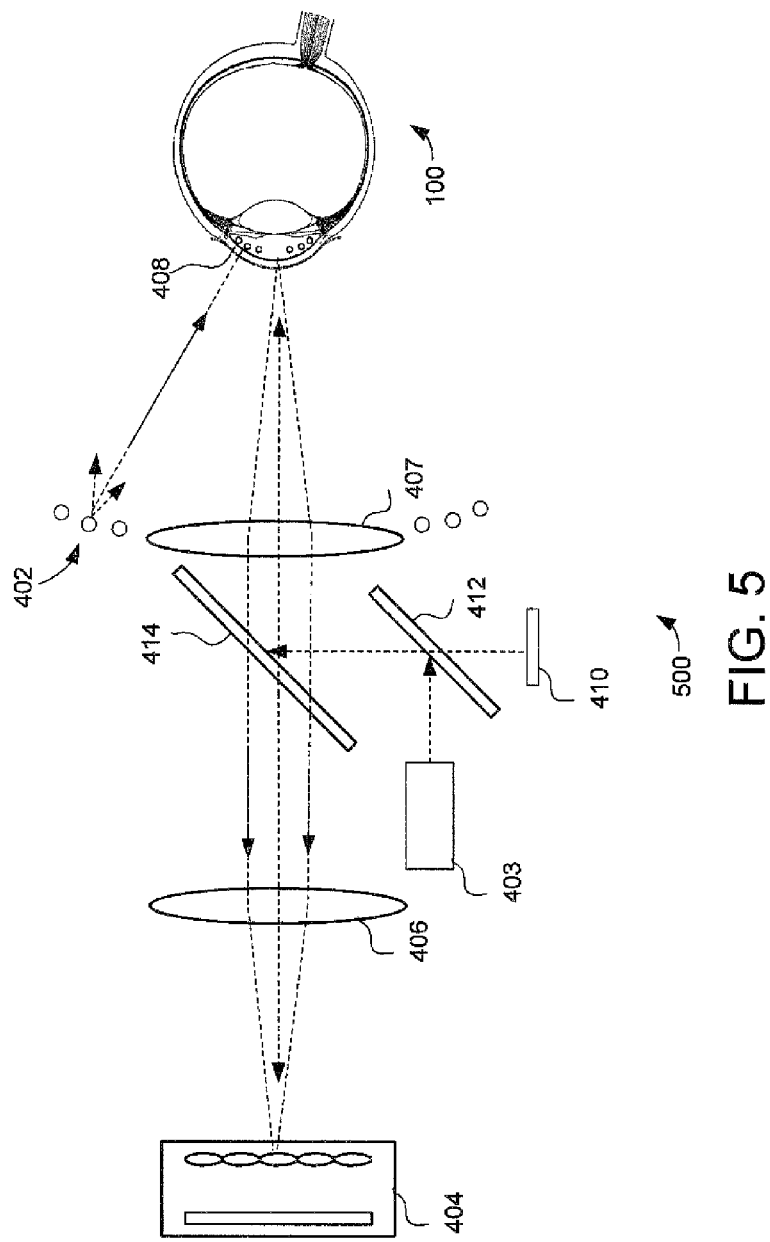

Turning now to FIG. 5, a simplified schematic view of a second ocular topography and aberrometry system 500 is illustrated. Like system 400, the system 500 includes a first set of light sources 402, a second light source 403, a plenoptic detector 404, a lens 406, a target 410, a first beam splitter 412 and a second beam splitter 414. However, this embodiment includes a second lens 407, and with the two lenses arranged in a telocentric configuration. It should be noted that in this illustrated embodiment the eye 100 is one focal length from the second lens 407.

Positioning the eye 100 at one focal length from the second lens 407 is an unconventional configuration for a plenoptic detector. Specifically, such a configuration can result in reduced depth information from the plenoptic detector. However, such depth information can be increased using larger lenses 406 and 407 along with a large telocentric stop, possibly with wavelength dependence with radius.

Figure 6:
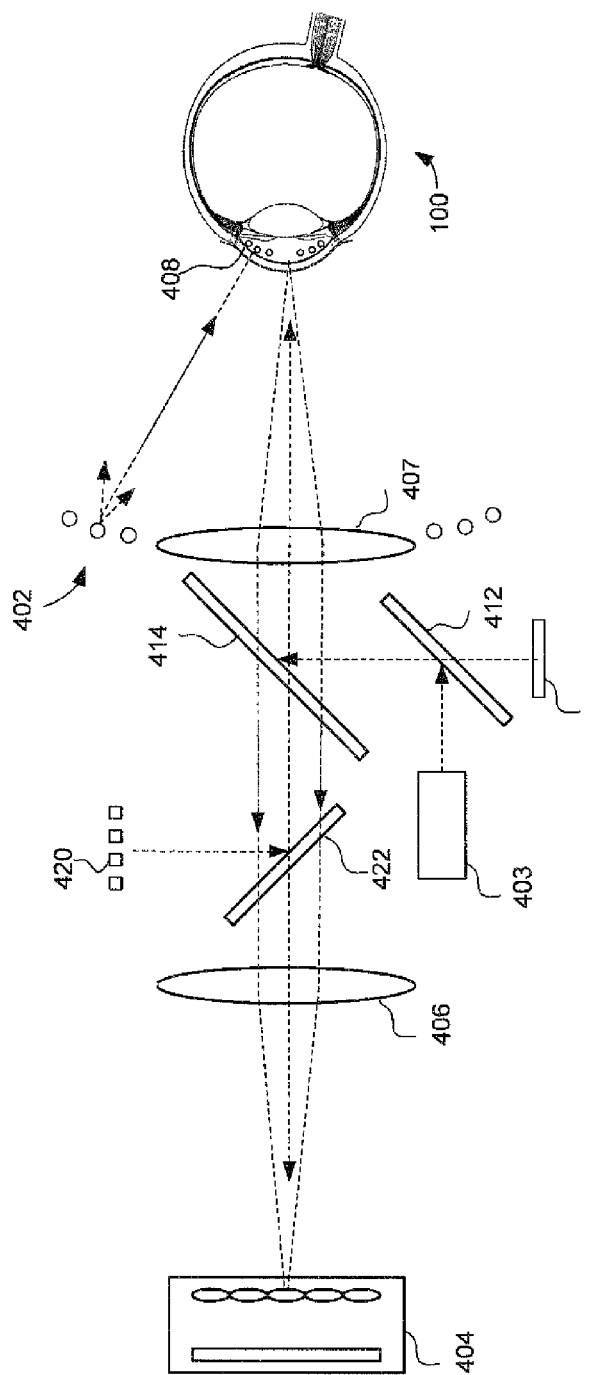

Turning now to FIG. 6, a simplified schematic view of a third ocular topography and aberrometry system 600 is illustrated. Like system 500, the system 600 includes a first set of light sources 402, a second light source 403, a plenoptic detector 404, a first lens 406, a second lens 407, a target 410, a first beam splitter 412 and a second beam splitter 414. However, this embodiment includes a Helmholtz light source 420 and a third beam splitter 422. It should be noted that in this illustrated embodiment the eye 100 is one focal length from the second lens 407.

In general, the Helmholtz light source 420 can be used to provide better measurements of ocular topography and aberrometry near the center of the eye 100. As one example, the Helmholtz light source 420 comprises a plurality of second elements or light sources that are optically located at a distance from the lens 406 that is equal to one focal length of the second lens 407. The Helmholtz light source 420 can comprise any source of electromagnetic radiation. The Helmholtz light source 420 is configured to reflect light off a beam splitter 422, and then to transmit the reflected light through the lens 407 and off a surface of the eye 100. The light reflected from a surface of the eye is passed back to the plenoptic detector 404. As more detailed examples, the Helmholtz light source 602 can comprise a plurality of individual light sources (e.g. LED light sources), a plurality of apertures in an opaque mask that is illuminated from behind the mask, or the like. As one example, the Helmholtz light source 420 can include a plurality of Helmholtz common elements having a common form and a Helmholtz reference element that is different than the common form.

As used herein, the term "Helmholtz source" or "Helmholtz light source" means one or a plurality of individual sources disposed such that light from each of the individual light sources passes through an optical element having optical power, reflects off of a test object, passes through the optical element, and is received by a detector, such as the plenoptic detector 404. In general, it is a characteristic of Helmholtz sources that the signal at the detector is independent of the position of the test object relative to the Helmholtz source.

The beam splitter 422 is configured to reflect light from the Helmholtz light source 420 through the lens 407 and to the eye 100. Like the light from the light sources 402, the light from the Helmholtz light source 420 forms images on the surfaces of the eye that are reflected back to the plenoptic detector 404. In this embodiment the Helmholtz light source 420 is used to provide more accurate measurements of ocular topography and aberrometry for portions of the eye 100 near the center. Specifically, because of their position, the light sources 402 may be limited in ability to form images on surfaces in the center portions of the eye, and thus the accuracy of the topography and aberrometry based on those images may be limited for the center portions of the eye 100. Thus, the addition of the Helmholtz light source 602 and beam splitter 604 may provide more complete topography and aberrometry of the eye.

To facilitate determining ocular topography and aberrometry using the images formed by the Helmholtz light source 420, the processing system can again computationally focus the various images created by the Helmholtz light source 602 and thus determine the parameters that result in these images being focused.

Furthermore, the Helmholtz light source 420 can be used to determine the distance to the eye 100. Again, such a distance can be used to calculate the directional information provided by the plenoptic detector. Furthermore, the distance can be calculated using ordinary image data of the light source 420.

Figure 7:
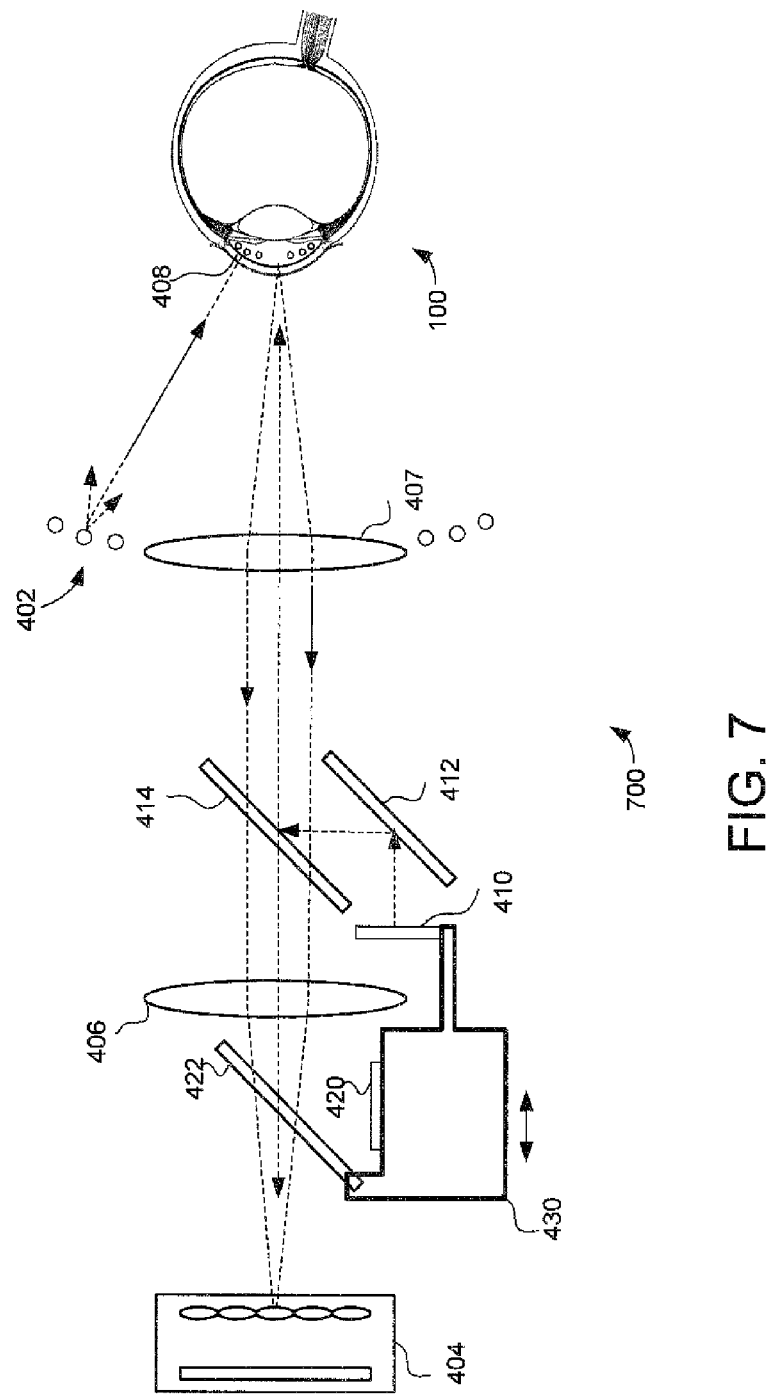

Turning now to FIG. 7, a simplified schematic view of a fourth ocular topography and aberrometry system 700 is illustrated. Like system 600 the system 700 includes a first set of light sources 402, a second light source 403, a plenoptic detector 404, a first lens 406, a second lens 407, a target 410, a first beam splitter 412, a second beam splitter 414, a Helmholtz light source 420 and a third beam splitter 422. It should be noted that in this illustrated embodiment the eye 100 is one focal length from the second lens 407. In this embodiment the mechanism 430 allows the attached elements to move, thus accommodating a wider range of different sized eyes.

As described above, the plenoptic detector 404 captures plenoptic image data that includes one or more of such Purkinje images. In one embodiment, the processing system is configured to determine the distances between the surfaces these Purkinje images are reflected from. For example, the processing system can be configured to computationally focus the plenoptic image data at the Purkinje I image, the Purkinje II image, the Purkinje III image, and the Purkinje IV image, and using the computational focusing, to calculate distances between the outer surface of the cornea in the eye 100, the inner surface of the cornea in the eye 100, the anterior surface of the lens in the eye 100, and the posterior surface of the lens in the eye 100. For example, the processing system can computationally focus the Purkinje III image, and thus determine the parameters that result in the Purkinje III image being focused. Then, the processing system can computationally focus the Purkinje IV image, and thus determine the parameters that result in the Purkinje IV image being focused. Then from these parameters the processing system can determine the depth of the focused images, and thus the distances between the focused images. Because the focused Purkinje III image corresponds to light reflected from an anterior surface of the lens, and the Purkinje IV image corresponds to light reflected from a posterior surface of the lens, the distance between focused images corresponds to the thickness of the lens. Similar procedures can be used with the other Purkinje images to determine other topography and aberrometry parameters in the eye. For example, to determine the thickness of the cornea, the depth of the anterior chamber, the distance between the lens and the cornea, etc.

Furthermore, similar procedures can be used to determine various radii of curvature in the eye. For example, by the determining how the focus parameters change at different positions along the Purkinje images, the radius of curvature of the associated surfaces can be determined. Thus, both the inner and outer radii of the cornea and the inner and outer radii of the lens can be determined.

Figure 8:
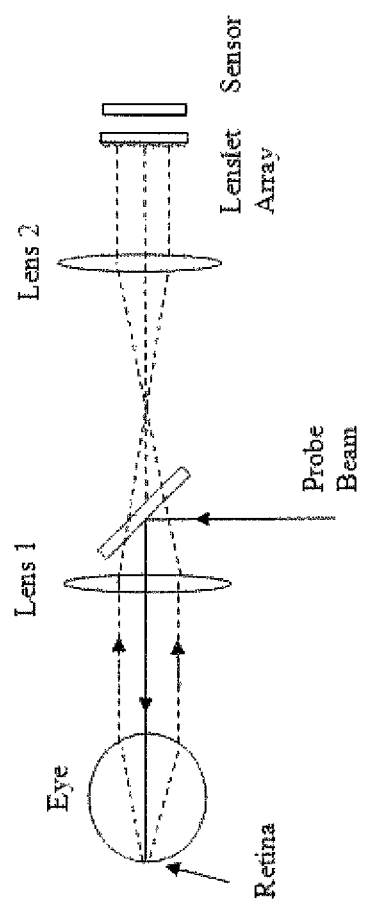
Figure 9:
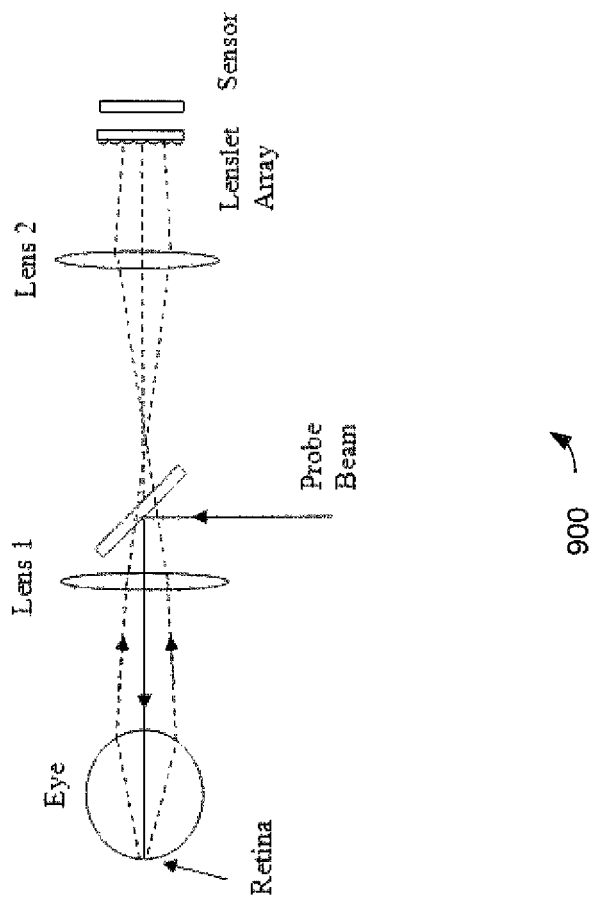

Turning now to FIGS. 8 and 9, a technique for aberrometry using a plenoptic detector is illustrated. In this illustrated example the spacing between the sensor and the lenslet array in the plenoptic detector is set to be equal to the focal length of the lenslet array. This means that if a collimated beam of light is incident on the lenslet array, a grid of equally spaced spots will form on the sensor of the plenoptic detector. Such a pattern, created with the collimated beam is called a "reference file" and is used in later calculations. If the beam hitting the lenslet array is a diverging spherical wave, the spots on the sensor will be spread out. If the beam is converging, the spots will be closer together. The amount of curvature of the beam can be calculated by analysis of the spot pattern as detected by the plenoptic detector. As one example, the process can be divided into three steps. The first step is to calculate the location of each spot under its corresponding lenslet. This first step is called centroiding. The second step is to calculate the slope at of the ray bundle that was hitting each lenslet. This is done by calculating the distance of the spot from a location that was recorded in the reference file. This process is called "calculating the slopes". The next step is called reconstruction. A perpendicular line segment drawn to each ray bundle to join them together into a continuous shape will generate a wavefront shape. Thus, to measure aberrometry of the eye the system illuminates the eye with a pattern, such as a pattern of spots. In FIG. 8, the pattern is illustrated as a thin probe beam of light that is sent into the eye. The thin beam hits the retina, and a small portion of the light from the retina reflects back out of the eye. In the example of FIG. 8 the eye has nearly perfect vision (an emmetrope). This is shown by the rays of light exiting the cornea. Specifically, the retina to cornea spacing is such that all the rays of light that exit the cornea are parallel. The rays then travel through lens 1, then lens 2 and then onto the lenslet array. In FIG. 8, the spacing between the lenses is the sum of the focal lengths. So the light rays that are collimated going into lens 2 are also collimated when they come out of lens 1 and strike the lenslet array. This creates a situation such that the spots that form on the retina will be in a regular grid with the spots all equally spaced (like they are in the reference file.). Thus, when the processing system reconstructs the image of the spots a determination can be made that the eye is emmetropic. For comparison, FIG. 9 shows the same system being used to measure a myope. In this situation, the eye is too long relative to the cornea. That makes the beam coming out of the eye converge, and results in the beam entering the lenslet array also converging, which makes the spots on the image move close together. Thus, when the processing system reconstructs the image of the spots a determination can be made that the eye is myopic based on the dimensions of the spots. Thus, topography and aberrometry can be combined into one instrument using the single plenoptic camera to perform both functions. For aberrometry measurement, the probe beam turns on and the topographer light turns off. For the topography measurement, the probe beam turns off and the topographer lights turn on.

One method to determine topography using a plenoptic detector is to treat the image from the camera as the same as an image captured by the conventional camera in a conventional topographer. For instance, most corneal topographers use a camera that has about one megapixel of resolution and this is sufficient to produce accurate corneal topography. Similarly, if a plenoptic camera has one million lenslets, it collects a conventional image that may be processed using the same topography reconstruction methods. Another method to determine topography using a plenoptic detector is to use the intensity and direction information that is provided by the detector. For example, the plenoptic data can be used to determine the distance from the detector to the camera and from this determine the base radius of the cornea. Specifically, once the distance is known, the reconstruction of the cornea base radius and overall shape may be done. Furthermore, it should be noted that by providing an accurate determination of distance, an accurate determination of final radius and shape calculations can be made. Specifically, with the plenoptic camera, the distance information is encoded directly in a single image so additional hardware is not required. For each point in the image, the plenoptic camera is able to calculate a distance beyond the light source. This allows for more accurate calculations of base radius and shape. Thus, plenoptic data can be used to determine topography by determining a distance to the cornea using the distance information encoded in the plenoptic image, and applying topographer reconstruction. In such a system, the range finding function of the Helmholtz source is being replaced by the plenoptic detector functionality. As a variation of the first method, the system may first render an image at a particular distance, and then process that image as a conventional image. This takes advantage of the characteristic of the plenoptic detector so that the operator does not have to precisely position the instrument in front of the eye for a good measurement to be taken. The processing system in essence performs the fine adjustment.

Another potential advantage is that the plenoptic detector allows the use of larger diameter aperture. In a conventional topographer, there is a small diameter aperture that limits the angle of light rays that reach the camera. This means that the area sampled on the cornea by each light source is small and, in fact, can be approximated as being essentially planar and independent of its neighbors. However, with a plenoptic camera, the aperture has a large diameter, allowing sampling of a larger region on the cornea. This allows the sampled areas to not be planar but instead have significant curvature. These regions of overlapping curvature may be combined using a reconstruction algorithm. Such a reconstruction algorithm may calculate the corneal shape with a spatial resolution that is finer than is possible with a conventional topographer. So the second method of calculating cornea shape would involve an iterative process where distance is simultaneously determined at the same time as the corneal shape. A variety of reconstruction methods are possible. An additional variation of the plenoptic topographer would be to allow a small aperture to be flipped into place while a second image was taken. The first image without the small aperture would be used for range finding. The second image with the aperture would be the one the topography was calculated from. Another variation of the plenoptic topographer would be for an optic to be placed in the system that had a wavelength selective coating. The coating would reflect some wavelengths and absorb others. So the effect of changing apertures would be accomplished by changing the illumination wavelengths. This has the advantage of replacing a mechanical movement with electrical switching, and as such can be accomplished more quickly and eliminate any potential movement of the eye between the images.

The embodiments described herein thus provide techniques for accurate determination of ocular topography and aberrometry. Such techniques can be used for any ophthalmic procedure requiring accurate determinations. These techniques can thus be used to improve the effectiveness of a wide variety of different ophthalmic procedures.

This disclosure has been provided in an exemplary form with a certain degree of particularity, and describes the best mode contemplated of carrying out the invention to enable a person skilled in the art to make or use embodiments of the invention. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. An ocular aberrometry and topography system, the aberrometry and topography system comprising:
   a first set of light sources configured to selectively illuminate an eye;
   a second light source configured to selectively illuminate the eye; a third light source configured to selectively illuminate the eye, wherein the third light source comprises a Helmholtz source;
   a plenoptic detector configured to selectively:
      receive images of the first set of light sources reflected from a corneal surface of the eye and generate first plenoptic image data representing the images of the first set of light sources;
      receive images of the second light source reflected from a retina of the eye and generate second plenoptic image data representing the images of the second light source;
   a processing system coupled to the plenoptic detector, the processing system configured to selectively:
      analyze the first plenoptic image data to determine topography for the eye; and
      analyze the second plenoptic image data to determine aberrometry for the eye.

2. The system of claim 1 wherein the plenoptic image detector comprises:

a photosensor array, the photosensor array comprising a plurality of photosensors; and a microlens array, the microlens array comprising a plurality of lenslets configured to direct the image to the photosensor array, the microlens array arranged a predetermined distance from the photosensor array.

3. The system of claim 2 wherein the photosensor array comprises a two dimensional array of photosensors, and wherein the microlens array comprises a two dimensional array of lenslets.

4. The system of claim 2 wherein each lenslet in the microlens array receives light from the eye at different angles and spatially separates the light at different angles at the detector.

5. The system of claim 2 wherein each lenslet in the microlens array is configured such that light arriving at a point in different directions is directed at a different point on the photosensor array such that direction information for light ray can be determined from a position of the light ray.

6. The system of claim 1 wherein the processing system is configured to analyze the first plenoptic image data to determine topography for the eye by calculating dimensions of shapes in the images of the first set of light sources reflected from the corneal surface of the eye.

7. The system of claim 1 wherein the processing system is configured to analyze the first plenoptic image data to determine topography for the eye by calculating a distance to the corneal surface using depth information generated from the first plenoptic image data.

8. The system of claim 1 wherein the processing system is configured to analyze the first plenoptic image data to determine topography for the eye by calculating a distance to the corneal surface using depth information generated from the first plenoptic image data and using the calculated distance to determine a base radius of the corneal surface.

9. The system of claim 1 wherein the processing system is configured to analyze the first plenoptic image data to determine topography by reconstructing a shape of the cornea from the plenoptic image data.

10. The system of claim 1 wherein the processing system is configured to analyze the first plenoptic image data to determine topography for the eye by using a first image taken with a small aperture and calculating a distance to the corneal surface using depth information generated from the first plenoptic image data of the first image, and by using a second image taken without the small aperture to reconstruct a shape of the cornea.

11. The system of claim 1 wherein the processing system is configured to analyze the second plenoptic image data to determine aberrometry for the eye by calculating angles of light emanating from the eye using the second plenoptic image data.

12. The system of claim 1 wherein the processing system is configured to analyze the second plenoptic image data to determine aberrometry for the eye by using direction information in the second plenoptic image data to determine angles of light emanating from the eye.

13. The system of claim 1 wherein the processing system is configured to analyze the second plenoptic image data to determine aberrometry for the eye by calculating dimensions of shapes in the images second light sources.

14. The system of claim 1 wherein the first set of light sources comprises a Placido-type light source.

15. The system of claim 1 wherein the first set of light sources comprises a pattern of shapes arranged in a grid.

16. The system of claim 1 wherein the first set of light sources comprises a pattern that includes a plurality of common elements and at least one reference element.

17. The system of claim 1 wherein the second light source comprises a super luminescent diode (SLD).

18. A method for determining ocular aberrometry and topography, comprising:
    selectively illuminate an eye with a first set of light sources;
    receiving images of the first set of light sources reflected from a corneal surface of the eye;
    generating first plenoptic image data representing the images of the first set of light sources;
    analyzing the first plenoptic image data to determine topography for the eye;
    selectively illuminating the eye with a second light source;
    receiving images of the second light source reflected from a retina of the eye;
    generating second plenoptic image data representing the images of the second light source; and
    analyzing the second plenoptic image data to determine aberrometry for the eye; further comprising a third light source configured to selectively illuminate the eye, wherein the third light source comprises a Helmholtz source.

19. The method of claim 18 wherein the plenoptic image detector comprises:
    a photosensor array, the photosensor array comprising a plurality of photosensors; and
    a microlens array, the microlens array comprising a plurality of lenslets configured to direct the image to the photosensor array, the microlens array arranged a predetermined distance from the photosensor array.

20. The method of claim 19 wherein the photosensor array comprises a two dimensional array of photosensors, and wherein the microlens array comprises a two dimensional array of lenslets.

21. The method of claim 19 wherein each lenslet in the microlens array receives light from the eye at different angles and spatially separates the light at different angles at the detector.

22. The method of claim 19 wherein each lenslet in the microlens array is configured such that light arriving at a point in different directions is directed at a different point on the photosensor array such that direction information for light ray can be determined from a position of the light ray.

23. The method of claim 18 wherein the processing system is configured to analyze the first plenoptic image data to determine topography for the eye by calculating dimensions of shapes in the images of the first set of light sources reflected from the corneal surface of the eye.

24. The method of claim 18 wherein the analyzing the first plenoptic image data to determine topography for the eye comprises calculating a distance to the corneal surface using depth information generated from the first plenoptic image data.

25. The method of claim 18 wherein analyzing the first plenoptic image data to determine topography for the eye comprises calculating a distance to the corneal surface using depth information generated from the first plenoptic image data and using the calculated distance to determine a base radius of the corneal surface.

26. The method of claim 18 wherein the analyzing the first plenoptic image data to determine topography comprises reconstructing a shape of the cornea from the plenoptic image data.

27. The method of claim 18 wherein analyzing the first plenoptic image data to determine topography for the eye comprises using a first image taken with a small aperture and calculating a distance to the conical surface using depth information generated from the first plenoptic image data of the first image, and by using a second image taken without the small aperture to reconstruct a shape of the cornea.

28. The method of claim 18 wherein the analyzing the second plenoptic image data to determine aberrometry for the eye comprises calculating angles of light emanating from the eye using the second plenoptic image data.

29. The method of claim 18 wherein analyzing the second plenoptic image data to determine aberrometry for the eye comprises using direction information in the second plenoptic image data to determine angles of light emanating from the eye.

30. The method of claim 18 wherein analyzing the second plenoptic image data to determine aberrometry for the eye comprises calculating dimensions of shapes in the images second light sources.

31. The method of claim 18 wherein the first set of light sources comprises a Placido-type light source.

32. The method of claim 18 wherein the first set of light sources comprises a pattern of shapes arranged in a grid.

33. The method of claim 18 wherein the first set of light sources comprises a pattern that includes a plurality of common elements and at least one reference element.

34. The method of claim 18 wherein the second light source comprises a super luminescent diode (SLD).

* * * * *